(12) United States Patent
Hsieh (10) Patent No.: US 6,529,575 B1
(45) Date of Patent: Mar. 4, 2003

(54) ADAPTIVE PROJECTION FILTERING SCHEME FOR NOISE REDUCTION

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/063,485

(22) Filed: Apr. 29, 2002

(51) Int. Cl.[7] .................................................. A61B 6/00
(52) U.S. Cl. ........................................................ 378/4
(58) Field of Search .......................... 378/4, 8, 62, 901

(56) References Cited

U.S. PATENT DOCUMENTS 5,598,481 A * 1/1997 Nishikawa et al. ......... 128/925
5,715,334 A * 2/1998 Peters ........................ 382/130

* cited by examiner

Primary Examiner—David V. Bruce
(74) Attorney, Agent, or Firm—Cantor Colburn LLP (57) ABSTRACT

A method and system for reducing noise in an x-ray image generated by an imaging system using an adaptive projection filtering scheme including generating system information, obtaining original projection data, determining a data characteristic of the original projection data, processing the original projection data responsive to the system information and the data characteristic so as to create filtered projection data and calculating resulting projection data responsive to the filtered projection data. Also claimed is a medium encoded with a machine-readable computer program code for reducing noise in an x-ray image generated by an imaging system, the medium including instructions for causing controller to implement the aforementioned method.

31 Claims, 5 Drawing Sheets

ADAPTIVE PROJECTION FILTERING SCHEME FOR NOISE REDUCTION

BACKGROUND OF INVENTION

This invention relates generally to a method and system for reducing noise in an X-ray image and more particularly to a method and system for using an adaptive projection filtering scheme to reduce noise in an X-ray image generated by a Computed Tomography (CT) system.

In CT imaging systems, an x-ray source projects a fan-shaped beam that is collimated to lie within an X-Y plane, generally referred to as an "imaging plane", of a Cartesian coordinate system toward an array of radiation detectors, wherein each radiation detector includes a detector element disposed within the CT system so as to receive this fan-shaped beam. An object, such as a patient, is disposed between the x-ray source and the radiation detector array so as to lie within the imaging plane and so as to be subjected to the x-ray beam, which passes through the object. As the x-ray beam passes through the object, the x-ray beam becomes attenuated before impinging upon the array of radiation detectors. The intensity of the attenuated beam radiation received at the detector array is responsive to the attenuation of the x-ray beam by the object, wherein each detector element produces a separate electrical signal responsive to the beam intensity at the detector element location. These electrical signals are referred to as x-ray attenuation measurements or x-ray images.

Moreover, the x-ray source and the detector array may be rotated, with a gantry within the imaging plane, around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and the detector array. In an axial scan, the projection data is processed so as to construct an image that corresponds to a two-dimensional slice taken through the object. In CT systems that employ a single detector array, the slice thickness is controlled and determined by the width of the collimator, while in CT systems that employ a multiple detector array, the slice thickness is controlled and determined by summing the contributions of a plurality of detector sub-units and by physically moving the collimator to the outer edges of each slice.

With the introduction of high resolution (sub-mm) scanning and faster scan speeds, the peak and sustained CT system power requirements have increased dramatically. One reason for this is that higher resolution images require smaller slices. This effectively introduces additional signal loss due to gaps between individual cells and thus results in a significantly smaller number of detected x-ray photons. For example, the smallest slice thickness for an eight-slice scanner is 1.25 mm, wherein the smallest slice thickness for a sixteen-slice scanner is 0.625 mm. As such, assuming the same x-ray tube power, the number of detected x-ray photons for a sixteen-slice scanner will be more than a factor of two smaller than the number of detected x-ray photons for an eight-slice scanner.

One of the key obstacles in performing a smoothing operation to remove noise or statistical fluctuation is the ability to separate the real signal variation from the statistical fluctuation. If it is known prior to reconstruction that certain variations in the signal data is caused solely by statistical fluctuation, low-pass filters may be applied to the signal data without impacting the spatial resolution of the x-ray image. The key to differentiating between variations caused by the statistical fluctuations and the real signal variation or structure is the noise characteristic of the measured signal. In CT imaging, extensive pre-processing and calibration steps are performed to ensure artifact-free, or noise free, images. Unfortunately, the distribution of the statistical fluctuations following these steps is quite difficult to characterize.

SUMMARY OF INVENTION

The above discussed and other drawbacks and deficiencies are overcome or alleviated by a method for reducing noise in an x-ray image generated by a computed tomography imaging system using an adaptive projection filtering scheme comprising: generating system information; obtaining original projection data; determining a data characteristic of the original projection data; processing the original projection data responsive to the system information and the data characteristic so as to create filtered projection data and calculating resulting projection data responsive to the filtered projection data.

A medium encoded with a machine-readable computer program code for reducing noise in an x-ray image generated by a computed tomography imaging system using an adaptive projection filtering scheme, the medium including instructions for causing a controller to implement a method comprising: generating system information; obtaining original projection data; determining a data characteristic of the original projection data; processing the original projection data responsive to the system information and the data characteristic so as to create filtered projection data and calculating resulting projection data responsive to the filtered projection data.

A method for reducing noise in an image generated by an imaging system comprising: obtaining an imaging system and an object to be scanned; operating the imaging system so as to create original projection data responsive to the object; examining the original projection data so as to determine if the original projection data should be processed; and processing the original projection data using an adaptive projection filtering scheme wherein the filtering scheme, generates system information; determines a data characteristic of the original projection data; processes the original projection data responsive to the system information and the data characteristic so as to create filtered projection data and calculates resulting projection data responsive to the filtered projection data.

A system for reducing noise in an x-ray image comprising: a gantry having an x-ray source and a radiation detector array, wherein the gantry defines an object cavity and wherein the x-ray source and the radiation detector array are rotatingly associated with the gantry so as to be separated by the object cavity; a object support structure movingly associated with the gantry so as to allow communication with the object cavity; and a processing device having an adaptive projection filtering scheme, wherein the filtering scheme, generates system information; obtains original projection data; determines a data characteristic of the original projection data; processes the original projection data responsive to the system information and the data characteristic so as to create filtered projection data and calculates resulting projection data responsive to the filtered projection data.

A system for reducing noise in an image generated by an imaging system using an adaptive projection filtering scheme comprising: the imaging system; an object disposed so as to be communicated with the imaging system, wherein the imaging system generates original projection data responsive to the object; and a processing device, wherein the processing device, generates system information; obtains the original projection data; determines a data characteristic of the original projection data; processes the original projection data responsive to the system information and the data characteristic so as to create filtered projection data and calculates resulting projection data responsive to the filtered projection data.

The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures.

DETAILED DESCRIPTION

In accordance with an exemplary embodiment, while a method and system for reducing noise in an x-ray image generated by an imaging system using an adaptive projection filtering scheme is described and discussed hereinbelow with reference to a computed tomography (CT) imaging system, it should be understood that the method and system of the invention may be applied to other imaging systems, such as Magnetic Resonance Imaging (MRI).

Figure 1:
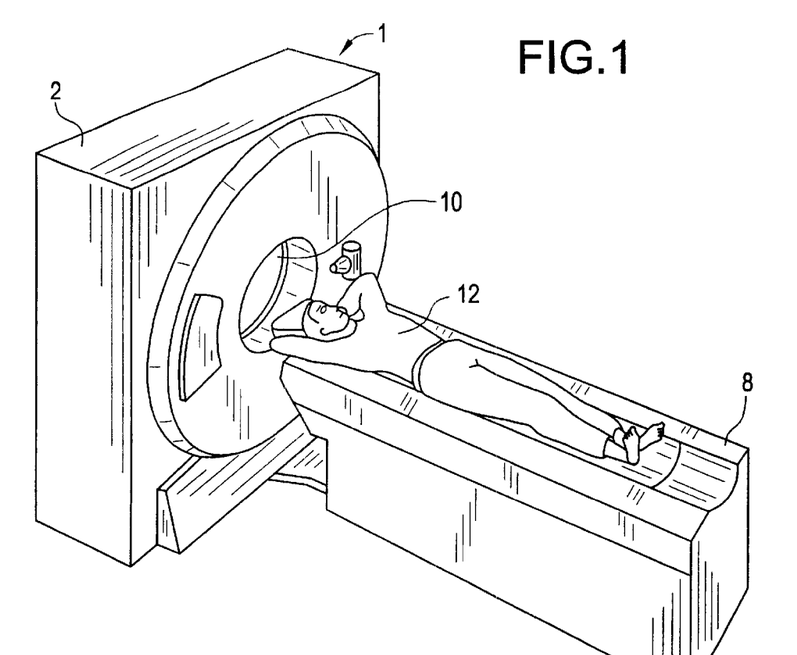
FIG. 1 is a perspective view of a CT imaging system and a patient disposed for imaging, in accordance with an exemplary embodiment.
Figure 2:
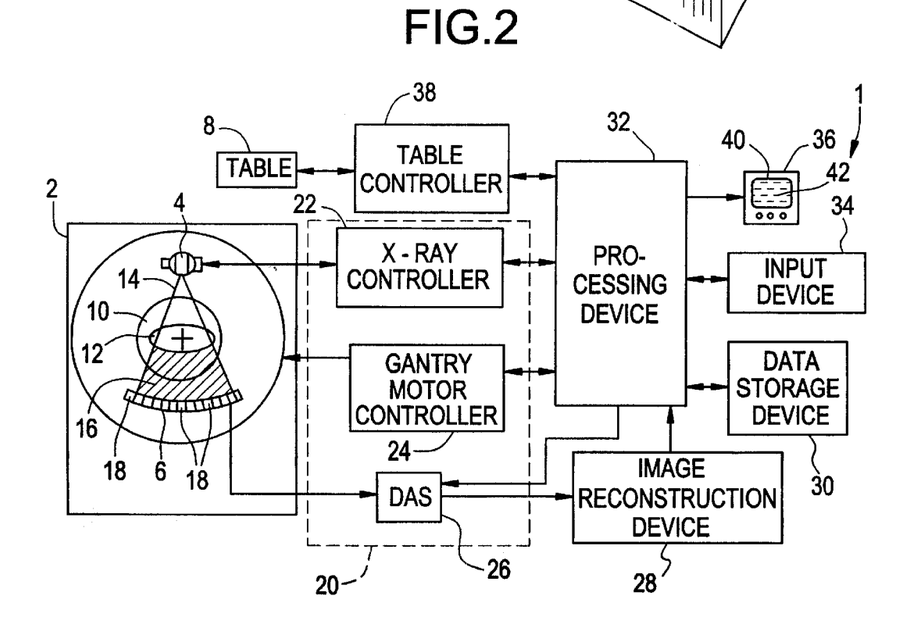
FIG. 2 is a block schematic diagram of a CT imaging system, in accordance with an exemplary embodiment.

Referring to FIG. 1 and FIG. 2 a representative CT imaging system 1 is shown and includes a gantry 2 having an x-ray source 4, a radiation detector array 6, a patient support structure 8 and a object cavity 10, wherein x-ray source 4 and radiation detector array 6 are opposingly disposed so as to be separated by object cavity 10. An object, such as a patient 12, is dispose upon patient support structure 8 which is then disposed within an object cavity 10. X-ray source 4 projects an x-ray beam 14 toward radiation detector array 6 so as to pass through patient 12. X-ray beam 14 is then collimated by a collimate so as to lie within an X-Y plane of a Cartesian coordinate system referred to as an "imaging plane". After passing through and becoming attenuated by patient 12, attenuated x-ray beam 16 is received by radiation detector array 6. Radiation detector array 6 includes a plurality of detector elements 18 wherein each of said detector elements 18 receives attenuated x-ray beam 16 and produces an electrical signal responsive to the intensity of attenuated x-ray beam 16.

In addition, x-ray source 4 and radiation detector array 6 are rotatingly disposed relative to gantry 2 and patient support structure 8, so as to allow x-ray source 4 and radiation detector array 6 to rotate around patient support structure 8 when patient support structure 8 is disposed within object cavity 10. X-ray projection data is obtained by rotating x-ray source 4 and radiation detector array 6 around patient 10 during a scan. X-ray source 4 and radiation detector array 6 are preferably communicated with a control mechanism 20 associated with CT imaging system 1. Control mechanism 20 controls the rotation and operation of x-ray source 4 and radiation detector array 6.

Control mechanism 20 includes an x-ray controller 22 communicated with x-ray source 4, a gantry motor controller 24, and a data acquisition system (DAS) 26 communicated with radiation detector array 6, wherein x-ray controller 22 provides power and timing signals to x-ray source 4, gantry motor controller 24 controls the rotational speed and angular position of x-ray source 4 and radiation detector array 6 and DAS 26 receives the electrical signal data produced by detector elements 18 and converts this data into digital signals for subsequent processing. CT imaging system 1 also includes an image reconstruction device 28, a data storage device 30 and a processing device 32, wherein processing device 32 is communicated with image reconstruction device 28, gantry motor controller 24, x-ray controller 22, data storage device 30, an input device 34 and an output device 36. Moreover, CT imaging system 1 also includes a table controller 38 communicated with processing device 32 and patient support structure 8, so as to control the position of patient support structure 8 relative to object cavity 10.

Patient 12 is preferably disposed on patient support structure 8, which is then positioned by an operator via processing device 32 so as to be disposed within object cavity 10. Gantry motor controller 24 is operated via processing device 32 so as to cause x-ray source 4 and radiation detector array 6 to rotate relative to patient 12. X-ray controller 22 is operated via processing device 32 so as to cause x-ray source 4 to emit and project a collimated x-ray beam 14 toward radiation detector array 6 and hence toward patient 12. X-ray beam 14 passes through patient 12 so as to create an attenuated x-ray beam 16, which is received by radiation detector array 6.

Detector elements 18 receive attenuated x-ray beam 16, produces electrical signal data responsive to the intensity of attenuated x-ray beam 16 and communicates this electrical signal data to DAS 26. DAS 26 then converts this electrical signal data to digital signals and communicates both the digital signals and the electrical signal data to image reconstruction device 28, which performs high-speed image reconstruction. This information is then communicated to processing device 32, which stores the image in data storage device 30 and displays the digital signal as an image via output device 36.

Figure 3:
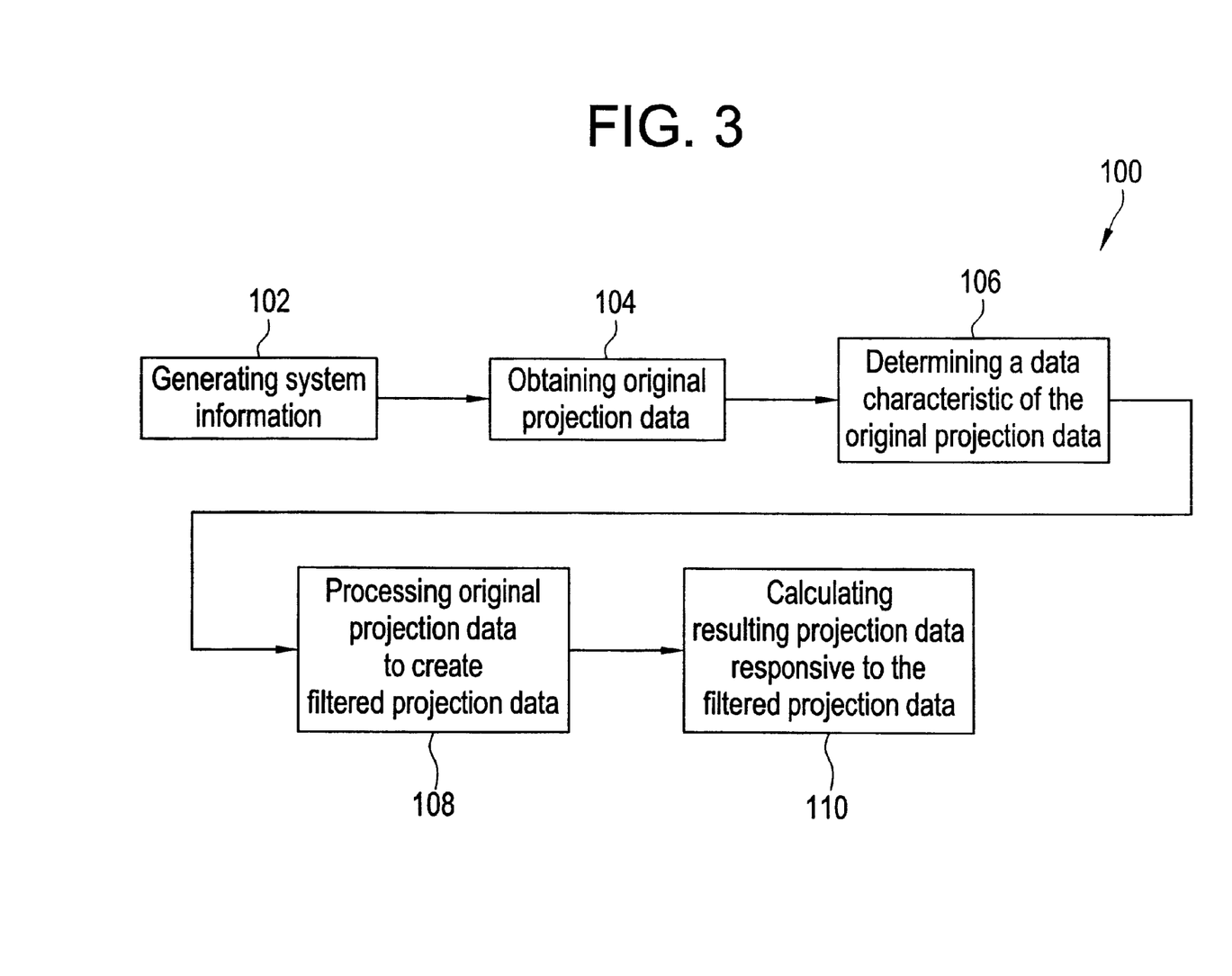
FIG. 3 is a flow diagram describing a method for reducing noise in a CT image using an adaptive projection filtering scheme, in accordance with an exemplary embodiment.

Referring to FIG. 3, a flow diagram describing a method for reducing noise in a CT image using an adaptive projection filtering scheme 100, is shown and discussed. In accordance with an exemplary embodiment, system information such as an air-cal vector and a bowtie vector is generated as shown in step 102. An air-cal vector (Aircal ($\gamma$)) responsive to the channel-to-channel gain variation and the shape of the bowtie filter is generated, wherein γ is the detector angle formed by radiation detector array 6 with the iso-ray. This is preferably accomplished by performing a series of scans using CT imaging system 1 without patient 12 being disposed within object cavity 10. The channel average intensity of the scan reading at each angle γ for each channel is obtained and the air-cal value for that angle γ and channel is determined by dividing a constant by the respective channel average intensity. The air-cal values for each channel at each angle γ constitute the air-cal vector (Aircal(γ)). It should be noted that this calculation should be performed for different collimator apertures, focal spot sizes, tube voltages and bowtie filter shapes. Because the air-cal vector is responsive to the channel-to-channel gain variation and the shape of the bowtie filter, this air-cal vector advantageously removes any influence contributed by the bowtie filter (such as non-uniformity of the input x-ray flux caused by the presence of the bowtie filter), as well as the channel-to-channel gain variations contributed by detector array 6 and/or DAS 26.

Once the air-cal vector has been determined a bowtie vector (B(γ)) is generated, wherein the bowtie vector estimates the bowtie effect produced by the bowtie filter. The bowtie vector is preferably generated by performing a polynomial fit of the air-cal vector, Aircal(γ), as given by:

$$B(\gamma)=\text{poly\_fit}(x^2, \text{Aircal}(\gamma)),$$

Wherein, x is the detector channel index of radiation detector array 6 with the iso-channel being zero and γ is the angle formed by the radiation detector array 6 with the iso-ray. Alternatively, $\gamma^2$ may be used in place of $x^2$ as an independent variable in the polynomial fit above. Although the bowtie vector is preferably generated as shown hereinabove and because the shape of the bowtie filter is known, the bowtie vector may also be estimated by theoretically calculating the path length and the attenuation of the bowtie filter as a function of detector angle γ. However, due to slight misalignments inherently present in CT imaging system 1 and because the attenuation coefficient changes as a function of the x-ray spectrum, calculation of a precise bowtie shape is difficult.

Once the air-cal vector and the bowtie vector have been generated as shown in step 102, original projection data (p(γ)) is obtained using CT imaging system 1, as shown in step 104. This may be accomplished by operating CT imaging system 1 so as to create original projection data representative of a patient 12 disposed within object cavity 10. This original projection data is then processed by processing device 32 so as to account for various operational characteristics, such as offset correction, primary speed correction and reference channel correction. In addition, while the original projection data is being obtained, a separate reference channel ($\gamma_0$) of CT imaging system 1 is being operated so as to obtain reference or normalization data, wherein the normalization data is separate from patient 12 and responsive to the operational characteristics of CT imaging system 1. This normalization data is used in the processing of the original projection data as discussed hereinabove.

Once these values have been obtained data characteristics of the original projection data may then be determined as shown in step 106. Although these data characteristics preferably include a calculated standard deviation, a high deviation threshold level, a low deviation threshold level and measured variation data, any other data characteristics suitable to the desired end purpose may be used.

Once these values have been obtained, a calculated standard deviation (σ(γ)) may then be calculated as given by:

$$\sigma(\gamma)=[B(\gamma)*(p(\gamma))^{1/2}]/[(p(\gamma_0))].$$

Wherein, B(γ) is the bowtie vector, p(γ) is the original projection data and $p(\gamma_0)$ is the normalization data obtained for reference channel $\gamma_0$. The standard deviation σ (γ) represents the estimation of variation in the original projection data due solely to statistical fluctuations. Once the standard deviation has been obtained, a high deviation threshold level, $t_{hi}$, and a low deviation threshold level, $t_{lo}$, are then determined in a manner responsive to the scanning technique employed (slice thickness, kV, mA, helical, pitch, etc).

Figure 4A:
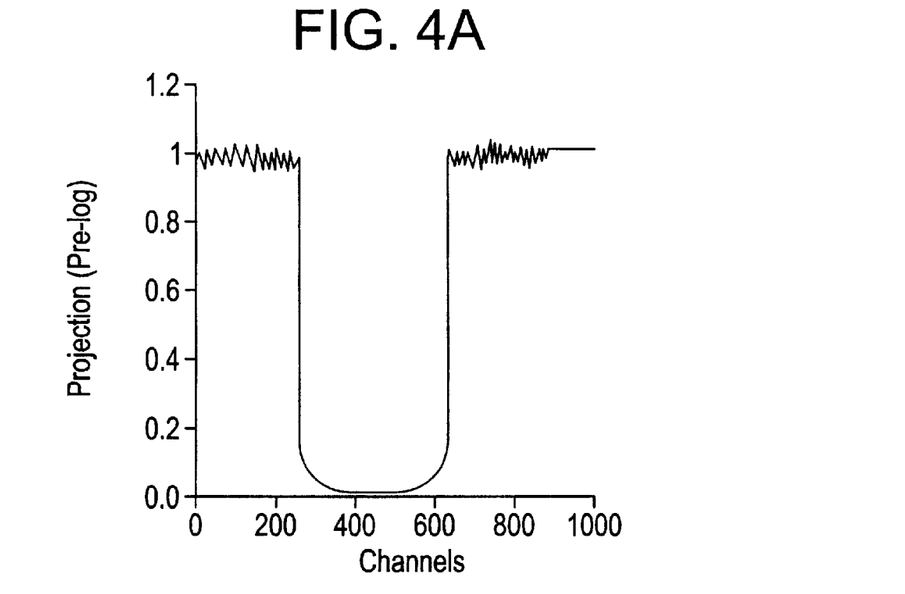
FIG. 4A is a graph showing image data for a QA phantom.
Figure 4B:
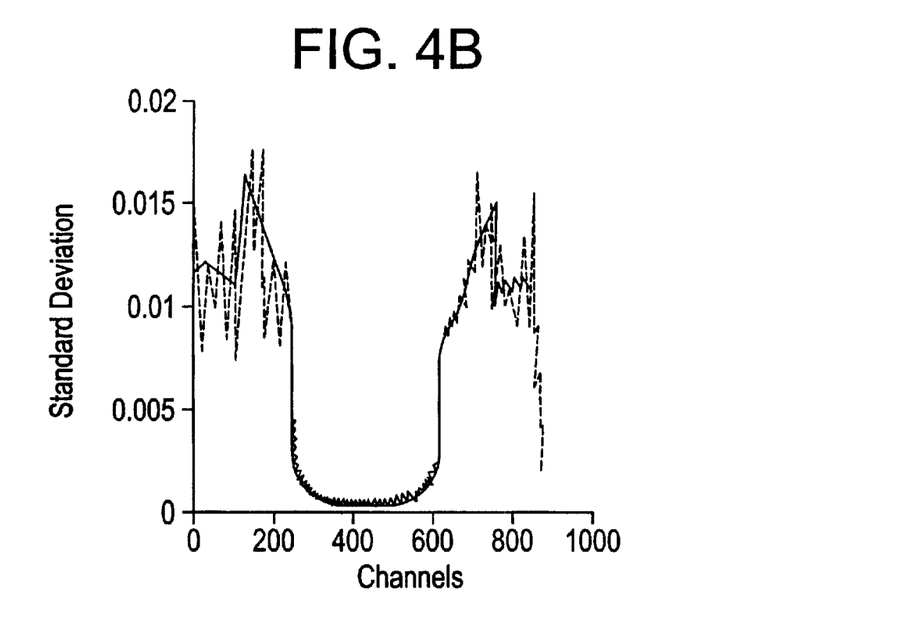
FIG. 4B is a graph showing the calculated standard deviation and the measured standard deviation of a QA phantom.

Referring to FIG. 4A and FIG. 4B, an example of projection data (e.g. a calibrated projection) and the corresponding calculated standard deviation for a QA phantom is shown, respectively. The calculated standard deviation, as calculated hereinabove, is shown as a solid line, whereas the corresponding measured variations are shown as a dotted line. It is clear that a nice agreement between the calculated standard deviation and the measured variation is advantageously obtained.

Figure 5:
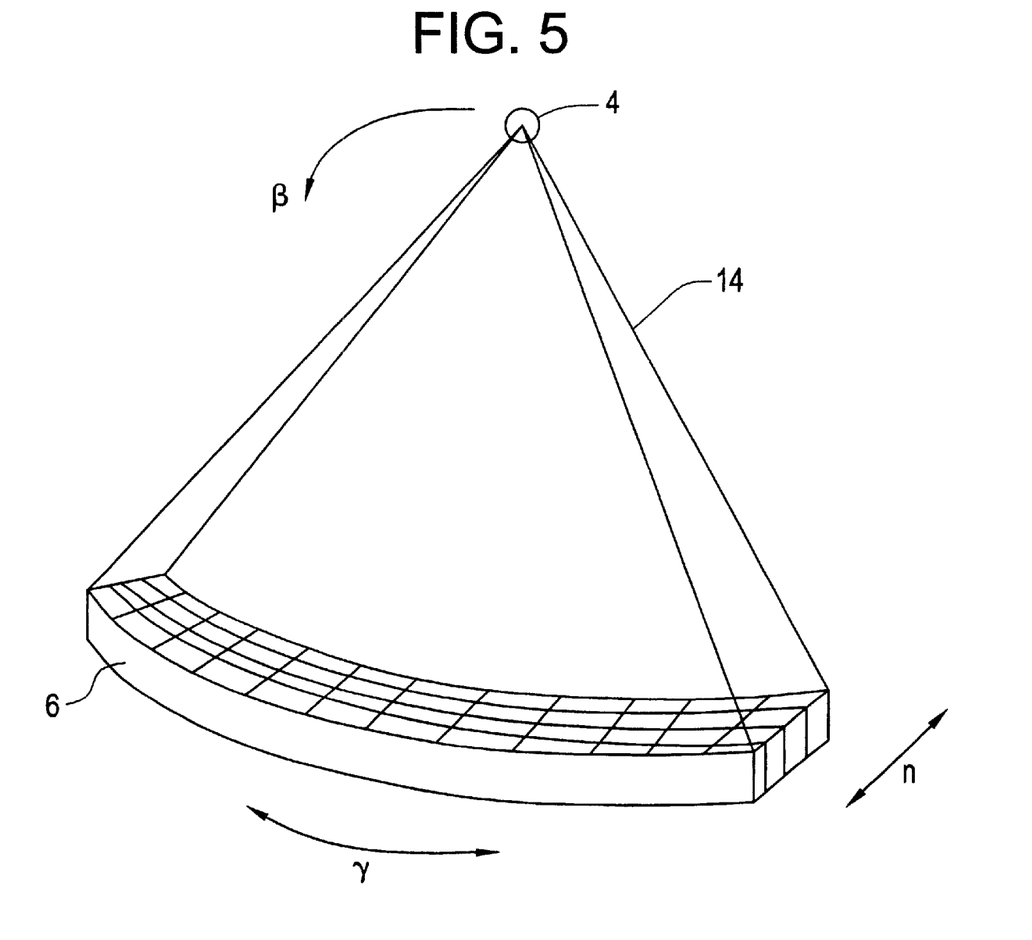
FIG. 5 is an example of an arrangement of an x-ray source, an x-ray beam and a radiation detector array.

Moreover, referring to FIG. 5, the original projection data is then processed so as to create measured variation data (ε(γ)). This measured variation data, which reduces the impact on the spatial resolution due to filtration of the real structure, may be calculated using the standard deviation for a small neighborhood or range of original projection data for a channel of interest and/or for different orientations, such as variance across detector channels γ, across views β, across detector rows n and/or other intermediate directions such as diagonal across both γ and β. To further reduce the impact on the spatial resolution of the original projection data due to filtration of the real structure, the standard deviation may be calculated for all orientations and the smallest variation may be selected as the measured variation data. Alternatively, the average of the smallest variation, as determined hereinabove, may also be selected as the measured variation data. It should be noted that as discussed hereinabove, p(γ) is used to identify the original projection data obtained via a detector channel in order to simplify the above explanation. In reality however, p (γ, β,n) should be used to identify the original projection data obtained via a detector channel, wherein, as above, γ represents the detector angle, β represents the projection angle and n represents the detector row.

Once the measured variation data is obtained, the original projection data is processed so as to create filtered projection data ($p_f(\gamma)$) as shown in step 108. This is preferably accomplished by first comparing the measured variation data with the calculated standard deviation together with the high deviation threshold level, $t_{hi}$, and the low deviation threshold level, $t_{lo}$. The original projection data may then processed in a manner responsive to the measured variation data. For example, if ε (γ)>σ(γ)$t_{hi}$, then no filtering or smoothing operation is performed on the original projection data since the measured variation most likely represents real object structures. In this case, the original projection data remains unchanged. However, if ε (γ)<σ(γ)$t_{lo}$, then a filtering or smoothing operation is performed on the original projection data so as to create filtered projection data and the original projection data is then replaced with the filtered projection data. Moreover, if σ(γ)$t_{hi}$,>ε(γ)>σ(γ)$t_{lo}$, then the amount of filtering applied to the original projection data may vary between these two extremes so as to create partially filtered projection data, as give by:

$$\frac{\sigma(\gamma)t_{hi} - \xi(\gamma)}{\sigma(\gamma)(t_{hi} - t_{lo})}.$$

As such, in view of the above discussion a weighting function ($\alpha(\gamma)$) may be generated such that the result is a linear combination of the original projection data and the filtered projection data. For example, $\alpha(\gamma)$ may be described by the following equation:

$$\alpha(\gamma) = \begin{cases} 1, & \xi(\gamma) \leq \sigma(\gamma)t_{lo} \\ \frac{\sigma(\gamma)t_{hi} - \xi(\gamma)}{\sigma(\gamma)(t_{hi} - t_{lo})}, & \sigma(\gamma)t_{lo} < \xi(\gamma) < \sigma(\gamma)t_{hi} \\ 0, & \xi(\gamma) \geq \sigma(\gamma)t_{hi} \end{cases}$$

It should be noted that the filtering operation discussed hereinabove, may also be selected along the same orientation as the measured variation data, so as to filter the original projection data along the direction of less variation in order to avoid real structures. In addition, the smoothing filter is preferably a low pass filter and may be any type of low pass filter or statistical based filter suitable to the desired end purpose.

Once the filtered projection $p_f(\gamma)$ is generated as in step 106, resulting projection data $p_r(\gamma)$ is calculated as shown in step 110, and may be calculated as given by:

$$p_r(\gamma) = p(\gamma) - \alpha(\gamma)[p(\gamma) - p_f(\gamma)].$$

Wherein, $p_f(\gamma)$ is the filtered projection data, $p(\gamma)$ is the original projection data and $\alpha(\gamma)$ is the weighting function as described hereinabove. The resulting projection data $p_r(\gamma)$ may then be stored in data storage device 30 and/or displayed as a resulting projection image.

It should be noted that although the filtered projection data $p_f(\gamma)$ is preferably obtained as described hereinabove, the filtered projection data may be obtained using any method, device or noise suppression technique suitable to the desired end purpose.

Figure 6:
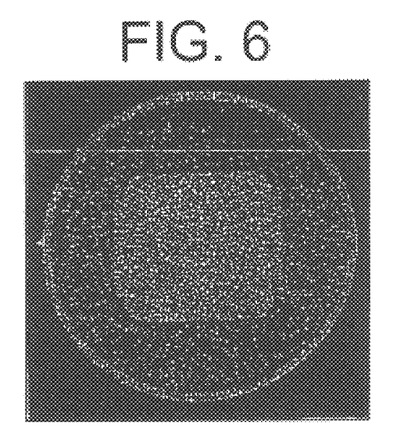
FIG. 6 shows a reconstructed image of a QA phantom using a conventional reconstruction technique.
Figure 7:
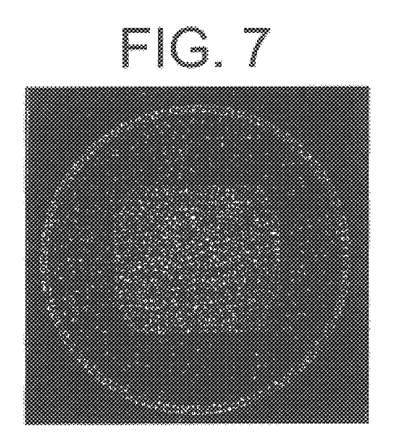
FIG. 7 shows a reconstructed image of a QA phantom using an adaptive projection filtering scheme, in accordance with an exemplary embodiment.
Figure 8:
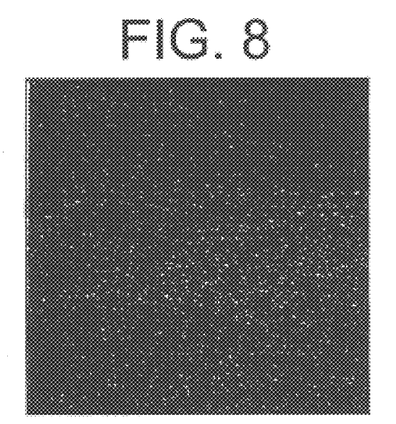
FIG. 8 shows a difference image illustrating the image difference between FIG. 6 and FIG. 7.

Application of an exemplary embodiment of the method and system discussed hereinabove advantageously reconstructs image data having significantly reduced image noise. This can be seen by referring to FIG. 6 and FIG. 7, wherein FIG. 6 illustrates a reconstructed image of a QA phantom using a conventional reconstruction technique and wherein FIG. 7 illustrates a reconstructed image of the same QA phantom using an adaptive projection filtering scheme, in accordance with an exemplary embodiment. FIG. 8 is a difference image illustrating the difference between FIG. 6 and FIG. 7. It should be noted that there is no structural information present in FIG. 8 which indicates that the adaptive projection filtering scheme 100 advantageously maintains and preserves the spatial resolution of the original projection data $p(\gamma)$.

In accordance with a first alternative embodiment, although a linear process was illustrated to generate the weighting function and the resulting projection, the weighting function and/or the resulting projection may be determined using non-linear processes and/or methods. In addition, the filtering operation as discussed hereinabove, may be dynamically adjusted in a manner responsive to the measured data. As such, if the noise variation is determined to be small, average filtered projection data for several orientations may be used to enhance the noise suppression capability.

In accordance with a second alternative embodiment, an iterative application of the above techniques discussed hereinabove may be applied. For example, once an image is reconstructed, the reconstructed image may be used as a guide for filtering of original projection data. This may be accomplished by calculating an object gradient variation based on the reconstructed image, wherein the gradient is the variation of the reconstructed object in different orientations. This estimated object gradient may then be used along with the standard deviation to guide the filtering process. This may provide an additional guideline for the filtering process by assuming that, if the local variation of the original projection data matches the gradient calculation, the measured variation is a real structure as opposed to noise.

In accordance with a third alternative embodiment, the high deviation threshold level and the low deviation threshold level may be dynamically adjusted in a manner responsive to the patient 12. For example, when an area that slowly varies is being scanned, the high deviation threshold level and the low deviation threshold level may be adjusted downward to further preserve the real structure or upward to improve the noise suppression. Additionally, these thresholds may be dynamically adjusted in a manner responsive to the modulation of the x-ray tube current. This is because to reduce the x-ray dosage, the tube current may change as a function of projection angle and/or scan location. As such, these threshold levels may be statically or dynamically modified to account for the changes in x-ray flux.

This invention advantageously allows imaging systems to scan and detect smaller anomalies and/or problems at an earlier stage, such as smaller tumors. This advantageously reduces the total amount of x-ray flux required to produce a clinically acceptable image quality and thus reduces the amount of x-ray dose received by patient 12. In addition, when applied under x-ray tube output limited conditions, this embodiment provides an improved image quality.

In accordance with an exemplary embodiment, adaptive projection filtering scheme 100 may be applied to acquired data obtained by any imaging system suitable to the desired end purpose, such as a magnetic resonance imaging (MRI) system.

In accordance with an exemplary embodiment, processing of FIG. 3 may be implemented through processing device 32 operating in response to a computer program. In order to perform the prescribed functions and desired processing, as well as the computations therefore (e.g., the execution of fourier analysis algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include signal input signal filtering to enable accurate sampling and conversion or acquisitions of such signals from communications interfaces. It is also considered within the scope of the invention that the processing of FIG. 3 may be implemented by a controller located remotely from processing device 32.

As described above, the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) can be updated to implement the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for reducing noise in an x-ray image generated by a computed tomography imaging system using an adaptive projection filtering scheme comprising:

generating system information;

obtaining original projection data;

determining a data characteristic of said original projection data;

processing said original projection data responsive to said system information and said data characteristic so as to create filtered projection data; and calculating resulting projection data responsive to said filtered projection data.

2. The method of claim 1, wherein said generating includes generating an air-cal vector, wherein said air-cal vector is responsive to the characteristics of the computed tomography imaging system.

3. The method of claim 2, wherein said generating includes calculating a bowtie vector so as to estimate the effect of a bowtie filter, wherein said bowtie vector is responsive to said air-cal vector.

4. The method of claim 1, wherein said obtaining includes operating a computed tomography imaging system so as to generate said original projection data, wherein said original projection data is responsive to an object being imaged.

5. The method of claim 1, wherein said obtaining includes processing said original projection data in a manner responsive to an offset correction, a primary speed correction and a reference channel correction.

6. The method of claim 1, wherein said obtaining includes operating a computed tomography imaging system having a reference channel so as to generate normalization data, wherein said normalization data is responsive to the characteristics of said reference channel.

7. The method of claim 1, wherein said determining includes determining a standard deviation responsive to said original projection data, normalization data and a bowtie vector.

8. The method of claim 7, wherein said determining includes determining a high deviation threshold level and a low deviation threshold level, wherein said high deviation threshold level and said low deviation threshold level is responsive to a scanning technique.

9. The method of claim 1, wherein said determining includes processing said original projection data so as to create measured variation data.

10. The method of claim 9, wherein said processing includes applying a smoothing filter to said original projection data so as to create said filtered projection data, wherein said filtered projection data is responsive to a high deviation threshold level, a low deviation threshold level and said measured variation data.

11. The method of claim 1, wherein said processing includes applying a smoothing filter to said original projection data for each channel of said computed tomography imaging system.

12. The method of claim 1, wherein said calculating includes calculating a weighting function responsive to said data characteristic and measured variation data.

13. The method of claim 1, wherein said calculating includes calculating said resulting projection data responsive to said original projection data, said filtered projection data and a weighting function.

14. A medium encoded with a machine-readable computer program code for reducing noise in an x-ray image generated by a computed tomography imaging system using an adaptive projection filtering scheme, said medium including instructions for causing a controller to implement a method comprising:

generating system information;

obtaining original projection data;

determining a data characteristic of said original projection data;

processing said original projection data responsive to said system information and said data characteristic so as to create filtered projection data; and calculating resulting projection data responsive to said filtered projection data.

15. The medium of claim 14, wherein said generating includes generating an air-cal vector, wherein said air-cal vector is responsive to the characteristics of the computed tomography imaging system.

16. The medium of claim 15, wherein said generating includes calculating a bowtie vector so as to estimate the effect of a bowtie filter, wherein said bowtie vector is responsive to said air-cal vector.

17. The medium of claim 14, wherein said obtaining includes operating a computed tomography imaging system so as to generate said original projection data, wherein said original projection data is responsive to an object being imaged.

18. The medium of claim 14, wherein said obtaining includes processing said original projection data in a manner responsive to an offset correction, a primary speed correction and a reference channel correction.

19. The medium of claim 14, wherein said obtaining includes operating a computed tomography imaging system having a reference channel so as to generate normalization data, wherein said normalization data is responsive to the characteristics of said reference channel.

20. The medium of claim 14, wherein said determining includes determining a standard deviation responsive to said original projection data, normalization data and a bowtie vector.

21. The medium of claim 20, wherein said determining includes determining a high deviation threshold level and a low deviation threshold level, wherein said high deviation threshold level and said low deviation threshold level is responsive to a scanning technique.

22. The medium of claim 14, wherein said determining includes processing said original projection data so as to create measured variation data.

23. The medium of claim 22, wherein said processing includes applying a smoothing filter to said original projection data so as to create said filtered projection data, wherein said filtered projection data is responsive to a high deviation threshold level, a low deviation threshold level and said measured variation data.

24. The medium of claim 14, wherein said processing includes applying a smoothing filter to said original projection data for each channel of said computed tomography imaging system.

25. The medium of claim 14, wherein said calculating includes calculating a weighting function responsive to said data characteristic and measured variation data.

26. The medium of claim 14, wherein said calculating includes calculating said resulting projection data responsive to said original projection data, said filtered projection data and a weighting function.

27. A method for reducing noise in an image generated by an imaging system comprising:

obtaining the imaging system and an object to be scanned;

operating the imaging system so as to create original projection data responsive to said object;

examining said original projection data so as to determine if said original projection data should be processed; and processing said original projection data using an adaptive projection filtering scheme wherein said filtering scheme, generates system information;

determines a data characteristic of said original projection data;

processes said original projection data responsive to said system information and said data characteristic so as to create filtered projection data; and calculates resulting projection data responsive to said filtered projection data.

28. A system for reducing noise in an x-ray image comprising:

a gantry having an x-ray source and a radiation detector array, wherein said gantry defines an object cavity and wherein said x-ray source and said radiation detector array are rotatingly associated with said gantry so as to be separated by said object cavity;

a object support structure movingly associated with said gantry so as to allow communication with said object cavity; and a processing device having an adaptive projection filtering scheme, wherein said filtering scheme, generates system information;

obtains original projection data;

determines a data characteristic of said original projection data;

processes said original projection data responsive to said system information and said data characteristic so as to create filtered projection data; and calculates resulting projection data responsive to said filtered projection data.

29. A system for reducing noise in an image generated by an imaging system using an adaptive projection filtering scheme comprising:

the imaging system;

an object disposed so as to be communicated with the imaging system, wherein the imaging system generates original projection data responsive to said object; and a processing device, wherein said processing device, generates system information;

obtains said original projection data;

determines a data characteristic of said original projection data;

processes said original projection data responsive to said system information and said data characteristic so as to create filtered projection data; and calculates resulting projection data responsive to said filtered projection data.

30. The system of claim 29, wherein said object is a patient.

31. The system of claim 29, wherein the imaging system is a computed tomography imaging system.

* * * * *

UNITED STATES PATENT AND TRADEMARK OFFICE
CERTIFICATE OF CORRECTION

PATENT NO. : 6,529,575 B1  
APPLICATION NO. : 10/063485  
DATED : March 4, 2003  
INVENTOR(S) : Jiang Hsieh

Page 1 of 1

It is certified that error appears in the above-identified patent and that said Letters Patent is hereby corrected as shown below:

<u>Column 5:</u>  
Line 30, delete "y 2" and insert therefor --$y^2$--  
Line 30, delete "x2" and insert therefor --$x^2$--

Signed and Sealed this

Fourteenth Day of November, 2006

JON W. DUDAS  
*Director of the United States Patent and Trademark Office*